(12) United States Patent
Podhajsky (10) Patent No.: US 7,648,503 B2
(45) Date of Patent: Jan. 19, 2010

(54) TISSUE COAGULATION METHOD AND DEVICE USING INERT GAS

(75) Inventor: Ronald J. Podhajsky, Boulder, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 587 days.

(21) Appl. No.: 11/370,287

(22) Filed: Mar. 8, 2006

(65) Prior Publication Data

US 2007/0213709 A1    Sep. 13, 2007

(51) Int. Cl.
A61B 18/14    (2006.01)
(52) U.S. Cl. .................................................... 606/49
(58) Field of Classification Search ............. 606/32–52
See application file for complete search history.

(56) References Cited

U.S. PATENT DOCUMENTS

| | | |
|---|---|---|
| 2,708,933 A | 5/1955 | August |
| 2,828,747 A | 4/1958 | August |
| 3,434,476 A | 3/1969 | Shaw et al. |
| 3,569,661 A | 3/1971 | Ebeling |
| 3,595,239 A | 7/1971 | Petersen |
| 3,692,973 A | 9/1972 | Oku et al. |
| 3,699,967 A | 10/1972 | Anderson |
| 3,832,513 A | 8/1974 | Klasson |
| 3,838,242 A | 9/1974 | Goucher |
| 3,903,891 A | 9/1975 | Brayshaw |
| 3,970,088 A | 7/1976 | Morrison |
| 3,987,795 A | 10/1976 | Morrison |
| 3,991,764 A | 11/1976 | Incropera et al. |
| 4,014,343 A | 3/1977 | Esty |
| 4,019,925 A | 4/1977 | Nenno et al. |
| 4,040,426 A | 8/1977 | Morrison, Jr. |
| 4,041,952 A | 8/1977 | Morrison, Jr. et al. |
| 4,043,342 A | 8/1977 | Morrison, Jr. |
| 4,057,064 A | 11/1977 | Morrison, Jr. et al. |
| 4,060,088 A * | 11/1977 | Morrison et al. .............. 606/49 |
| 4,209,018 A | 6/1980 | Meinke et al. |

(Continued)

FOREIGN PATENT DOCUMENTS

DE            3710489          11/1987

(Continued)

OTHER PUBLICATIONS

International Search Report EP 06 01 9572 dated Nov. 21, 2006.

(Continued)

*Primary Examiner*—Michael Peffley
*Assistant Examiner*—Ronald J Hupczey, Jr.

(57) ABSTRACT

A gas-enhanced electrosurgical method and apparatus for coagulating tissue. The apparatus includes a first tube with a proximal end and a distal end. The proximal end of the first tube is configured to receive pressurized ionizable gas. The distal end of the first tube is configured to deliver ionized gas towards a treatment area. The apparatus also includes at least one electrode positioned to selectively ionize the pressurized ionizable gas before the pressurized ionizable gas exits the distal end of the first tube. The electrode is adapted to operatively couple to an electrical energy source. The apparatus also includes a second tube with proximal and distal ends. The second tube is configured to selectively evacuate the ionized gas and dislodged tissue material from the treatment area.

6 Claims, 7 Drawing Sheets

U.S. PATENT DOCUMENTS

| | | | |
|---|---|---|---|
| 4,242,562 A | 12/1980 | Karinsky et al. |
| 4,311,145 A | 1/1982 | Esty et al. |
| 4,492,231 A | 1/1985 | Auth |
| 4,492,845 A | 1/1985 | Kljuchko et al. |
| 4,545,375 A | 10/1985 | Cline |
| 4,577,637 A | 3/1986 | Mueller, Jr. |
| 4,601,701 A | 7/1986 | Mueller, Jr. |
| 4,665,906 A | 5/1987 | Jervis |
| 4,708,137 A | 11/1987 | Tsukagoshi |
| 4,711,238 A | 12/1987 | Cunningham |
| 4,728,322 A | 3/1988 | Walker et al. |
| 4,732,556 A | 3/1988 | Chang et al. |
| 4,753,223 A | 6/1988 | Bremer |
| 4,781,175 A | 11/1988 | McGreevy et al. |
| 4,817,613 A | 4/1989 | Jaraczewski et al. |
| 4,822,557 A | 4/1989 | Suzuki et al. |
| 4,864,824 A | 9/1989 | Gabriel et al. |
| 4,890,610 A | 1/1990 | Kirwan, Sr. et al. |
| 4,901,719 A | 2/1990 | Trenconsky et al. |
| 4,901,720 A | 2/1990 | Bertrand |
| 4,931,047 A | 6/1990 | Broadwin et al. |
| 4,955,863 A | 9/1990 | Walker et al. |
| 5,015,227 A | 5/1991 | Broadwin et al. |
| 5,041,110 A | 8/1991 | Fleenor |
| 5,061,268 A | 10/1991 | Fleenor |
| 5,061,768 A | 10/1991 | Kishimoto et al. |
| 5,067,957 A | 11/1991 | Jervis |
| 5,088,997 A | 2/1992 | Delahuerga et al. |
| 5,098,430 A | 3/1992 | Fleenor |
| 5,108,389 A | 4/1992 | Cosmescu |
| RE33,925 E | 5/1992 | Bales et al. |
| 5,122,138 A | 6/1992 | Manwaring |
| D330,253 S | 10/1992 | Burek |
| 5,152,762 A | 10/1992 | McElhenney |
| 5,160,334 A | 11/1992 | Billings et al. |
| 5,163,935 A | 11/1992 | Black et al. |
| 5,195,959 A | 3/1993 | Smith |
| 5,195,968 A | 3/1993 | Lundquist et al. |
| 5,207,675 A | 5/1993 | Canady |
| 5,217,457 A | 6/1993 | Delahuerga et al. |
| 5,234,457 A | 8/1993 | Andersen |
| 5,242,438 A | 9/1993 | Saadatmonesh et al. |
| 5,244,462 A | 9/1993 | Delahuerga et al. |
| 5,248,311 A | 9/1993 | Black et al. |
| 5,256,138 A | 10/1993 | Burek et al. |
| RE34,432 E | 11/1993 | Bertrand |
| 5,292,320 A | 3/1994 | Black et al. |
| 5,306,238 A | 4/1994 | Fleenor |
| 5,324,283 A | 6/1994 | Heckele |
| 5,330,469 A | 7/1994 | Fleenor |
| RE34,780 E | 11/1994 | Trenconsky et al. |
| 5,366,456 A | 11/1994 | Rink et al. |
| 5,370,649 A | 12/1994 | Gardetto et al. |
| 5,380,317 A | 1/1995 | Everett et al. |
| 5,389,390 A | 2/1995 | Kross |
| 5,476,461 A | 12/1995 | Cho et al. |
| 5,496,308 A | 3/1996 | Brown et al. |
| 5,537,499 A | 7/1996 | Brekke |
| 5,620,439 A | 4/1997 | Abela et al. |
| 5,653,689 A | 8/1997 | Buelna et al. |
| 5,662,621 A | 9/1997 | Lafontaine |
| 5,669,904 A | 9/1997 | Platt, Jr. et al. |
| 5,669,907 A | 9/1997 | Platt, Jr. et al. |
| 5,688,261 A | 11/1997 | Amirkhanion et al. |
| 5,700,260 A | 12/1997 | Cho et al. |
| 5,716,365 A | 2/1998 | Goicoechea et al. |
| 5,720,745 A * | 2/1998 | Farin et al. ............ 606/49 |
| 5,782,860 A | 7/1998 | Epstein et al. |
| 5,782,896 A | 7/1998 | Chen et al. |
| 5,797,920 A | 8/1998 | Kim |
| 5,800,500 A | 9/1998 | Spelman et al. |
| 5,800,516 A | 9/1998 | Fine et al. |
| 5,821,664 A | 10/1998 | Shahinpoor |
| 5,836,944 A | 11/1998 | Cosmescu |
| 5,848,986 A | 12/1998 | Lundquist et al. |
| 5,855,475 A | 1/1999 | Fujio et al. |
| 5,908,402 A | 6/1999 | Blythe |
| 5,964,714 A | 10/1999 | Lafontaine |
| 5,972,416 A | 10/1999 | Reimels et al. |
| 6,039,736 A | 3/2000 | Platt |
| 6,080,183 A | 6/2000 | Tsugita et al. |
| 6,102,940 A | 8/2000 | Robichon et al. |
| 6,117,167 A | 9/2000 | Goicoechea et al. |
| 6,119,648 A | 9/2000 | Araki |
| 6,139,519 A | 10/2000 | Blythe |
| 6,149,648 A * | 11/2000 | Cosmescu ............ 606/42 |
| 6,197,026 B1 | 3/2001 | Farin et al. |
| 6,213,999 B1 | 4/2001 | Platt, Jr. et al. |
| 6,264,650 B1 | 7/2001 | Hovda et al. |
| 6,348,051 B1 | 2/2002 | Farin et al. |
| 6,458,125 B1 | 10/2002 | Cosmescu |
| 6,475,217 B1 | 11/2002 | Platt |
| 6,558,383 B2 | 5/2003 | Cunningham et al. |
| 6,602,249 B1 | 8/2003 | Stoddard |
| 6,616,660 B1 | 9/2003 | Platt |
| 6,666,865 B2 * | 12/2003 | Platt ..................... 606/49 |
| 6,852,112 B2 | 2/2005 | Platt |
| 6,911,029 B2 | 6/2005 | Platt |
| 7,033,353 B2 | 4/2006 | Stoddard |
| 2001/0018587 A1 | 8/2001 | Yamamoto |
| 2002/0022838 A1 | 2/2002 | Cunningham et al. |
| 2003/0093073 A1 | 5/2003 | Platt |
| 2003/0144654 A1 | 7/2003 | Hilal |
| 2004/0088029 A1 | 5/2004 | Yamamoto |
| 2004/0167512 A1 | 8/2004 | Stoddard |
| 2005/0015086 A1 | 1/2005 | Platt |
| 2005/0070894 A1 | 3/2005 | McClurken |
| 2005/0171528 A1 | 8/2005 | Sartor |
| 2005/0197658 A1 | 9/2005 | Platt |
| 2006/0052771 A1 | 3/2006 | Sartor |

FOREIGN PATENT DOCUMENTS

| | | |
|---|---|---|
| DE | 4139029 | 6/1993 |
| DE | 4326037 | 2/1995 |
| DE | 9117019 | 4/1995 |
| DE | 195 37 897 | 3/1997 |
| DE | 9117299 | 4/2000 |
| DE | 19848784 | 5/2000 |
| DE | 29724247 | 8/2000 |
| EP | 0 447 121 A2 | 9/1991 |
| EP | 0 612 535 | 8/1994 |
| EP | 956827 | 11/1999 |
| EP | 1 090 599 | 4/2001 |
| EP | 1 127 551 A1 | 8/2001 |
| EP | 1561430 | 8/2005 |
| EP | 1 570 798 A2 | 9/2005 |
| EP | 1 595 507 A2 | 11/2005 |
| FR | 1340509 | 9/1963 |
| GB | L014995 | 12/1965 |
| JP | 61-159953 | 7/1986 |
| SU | 1438745 | 11/1988 |
| WO | WO91/13593 | 9/1991 |
| WO | WO93/03678 | 3/1993 |
| WO | WO 96/02431 | 8/1996 |
| WO | WO96/27337 | 9/1996 |
| WO | WO99/15091 | 4/1999 |
| WO | WO 01/62333 | 8/2001 |
| WO | WO 02/058762 | 8/2002 |

WO   WO 2005/016142   2/2005

OTHER PUBLICATIONS

Grund et al., "Endoscopic Argon Plasma . . . Flexible Endoscopy" Endoscopic Surgery and Allied Technologies, No. 1, vol. 2, pp. 42-46 (Feb. 1994).

Farin et al., "Technology of Argon Plasma . . . Endoscopic Applications" Endoscopic Surgery and Allied Technologies, No. 1, vol. 2, pp. 71-77 (Feb. 1994).

Brand at al., "Electrosurgical Debulking of Ovarian Cancer: A New Technique Using the Argon Beam Coagulator" Gynecologic Oncology 39 pp. 115-118 (1990).

Hernandez et al., "A Controlled Study of the Argon Beam Coagultor for Partial Nephrectomy" The Journal of Urology, vol. 143, May (J. Urol. 143: pp. 1062-1065, 1990).

Ward et al., "A Significant New Contribution to Radical Head and Neck Surgery" Arch Otolaryngology, Head and Neck Surg., vol. 115 pp. 921-923 (Aug. 1989).

Mark H. Mellow, "The Role of Endoscopic Laser Therapy in Gastrointestinal Neoplasms" Advanced Therapeutic Endoscopy, pp. 17-21, 1990.

Silverstein et al., "Thermal Coagulation Therapy for Upper Gatrointestinal Bleeding" Advanced Therapeutic Endoscopy, pp. 79-84, 1990.

Waye et al., "Endoscopic Treatment Options" Techniques in Therapeutic Endoscopy, pp. 1.7-1.15, 1987.

International Search Report 01102843.8-2305, dated May 15, 2001.

International Searh Report PCT/US98/19284, dated Jan. 14, 1999.

European Search Report EP 05 00 2257, dated Jun. 1, 2005.

Extended European Search Report for European Patent Application No. EP 07 00 4356 dated Jul. 2, 2007 (7 pages).

* cited by examiner

TISSUE COAGULATION METHOD AND DEVICE USING INERT GAS

TECHNICAL FIELD

The present disclosure relates to gas-enhanced electrosurgical methods and devices. More particularly, the present disclosure relates to a gas-enhanced electrosurgical device and method for supplying gas to and removing gas from a surgical site.

BACKGROUND OF RELATED ART

Over the last several decades, more and more surgeons are abandoning traditional open methods of gaining access to vital organs and body cavities in favor of endoscopes and endoscopic instruments that access organs through small puncture-like incisions. Endoscopic instruments are inserted into the patient through a cannula, or a port that has been made with a trocar. Typical sizes for cannulas range from about three millimeters to about twelve millimeters. Smaller cannulas are usually preferred, and this presents a design challenge to instrument manufacturers who must find ways to make surgical instruments that fit through the cannulas and operate in a safe and effective manner.

Devices for arresting blood loss and coagulating tissue are well known in the art. For example, several prior art instruments employ thermic coagulation (heated probes) to arrest bleeding. However, due to space limitations, surgeons can have difficultly manipulating an instrument to coagulate, desiccate, fulgurate and/or cut tissue. Other instruments direct high frequency electric current through the tissue to stop the bleeding. Eschar adherence may also be a problem with these instruments. In both types of instruments, the depth of the coagulation is difficult to control.

Using these instruments to treat certain more sensitive tissue sites may be impractical since the constant and/or direct emission of ionized gas/plasma at the tissue may cause unintended results. Moreover, simply controlling the pressure of the gas from the source may not be effective or yield a desired result.

SUMMARY

The present disclosure relates to an electrosurgical apparatus and method for coagulating tissue. An electrosurgical apparatus includes a first tube with a proximal end and a distal end. The proximal end is configured to receive pressurized ionizable gas and the distal end is configured to deliver ionized gas towards a treatment area. The electrosurgical apparatus also includes at least one electrode positioned to selectively ionize the pressurized ionizable gas prior to the pressurized ionizable gas exiting the distal end of the first tube. The electrode is adapted to be operatively coupled to an electrical energy source. The electrosurgical apparatus also includes a second tube with proximal and distal ends. The second tube is configured to selectively evacuate the ionized gas and dislodged tissue material from the treatment area.

In one embodiment, the first tube is concentrically disposed within the second tube.

In an exemplary embodiment, the distal end of the first tube extends distally relative to the distal end of the second tube.

The electrode may be activated with a first electrical potential and the electrical energy source may include a remote patient pad that is energized to a second electrical potential.

In an embodiment of the disclosure, the electrosurgical apparatus is configured for use in a bipolar mode wherein the first tube is activated with a first electrical potential and the second tube is activated with a second electrical potential.

In an exemplary embodiment, the electrosurgical apparatus includes a regulator which regulates the flow of pressurized argon through the first tube. The regulator is disposed between a gas supply of the pressurized argon and the proximal end of the first tube.

In another embodiment of the disclosure, the electrosurgical apparatus includes a fluid agitator, which may be disposed within the first tube, to impart non-laminar flow characteristics to the pressurized ionizable gas. Here, the pressurized ionizable gas may be used to cool tissue.

The present disclosure also relates to an electrosurgical apparatus for coagulating tissue that is configured to use in a bipolar mode. In this embodiment, an electrode control mechanism that controls the current intensity to the electrode is disclosed.

The present disclosure also relates to a method for coagulating tissue. The method includes the steps of providing an electrosurgical apparatus including a first tube configured to receive pressurized ionizable gas and to deliver ionized gas towards a treatment area, at least one electrode positioned to selectively ionize pressurized ionizable gas prior to the pressurized ionizable gas exiting the first tube, and a second tube being configured to selectively evacuate the ionized gas and dislodged tissue material from the treatment area. The remaining steps include inserting the electrosurgical apparatus into tissue; delivering ionizable gas to the first tube; ionizing pressurized ionizable gas; delivering pressurized ionized gas through the first tube towards the treatment area; and removing pressurized ionized gas from the treatment area via the second tube. Additionally, a step of inserting an introducer into the tissue is disclosed.

DETAILED DESCRIPTION

Figure 1:
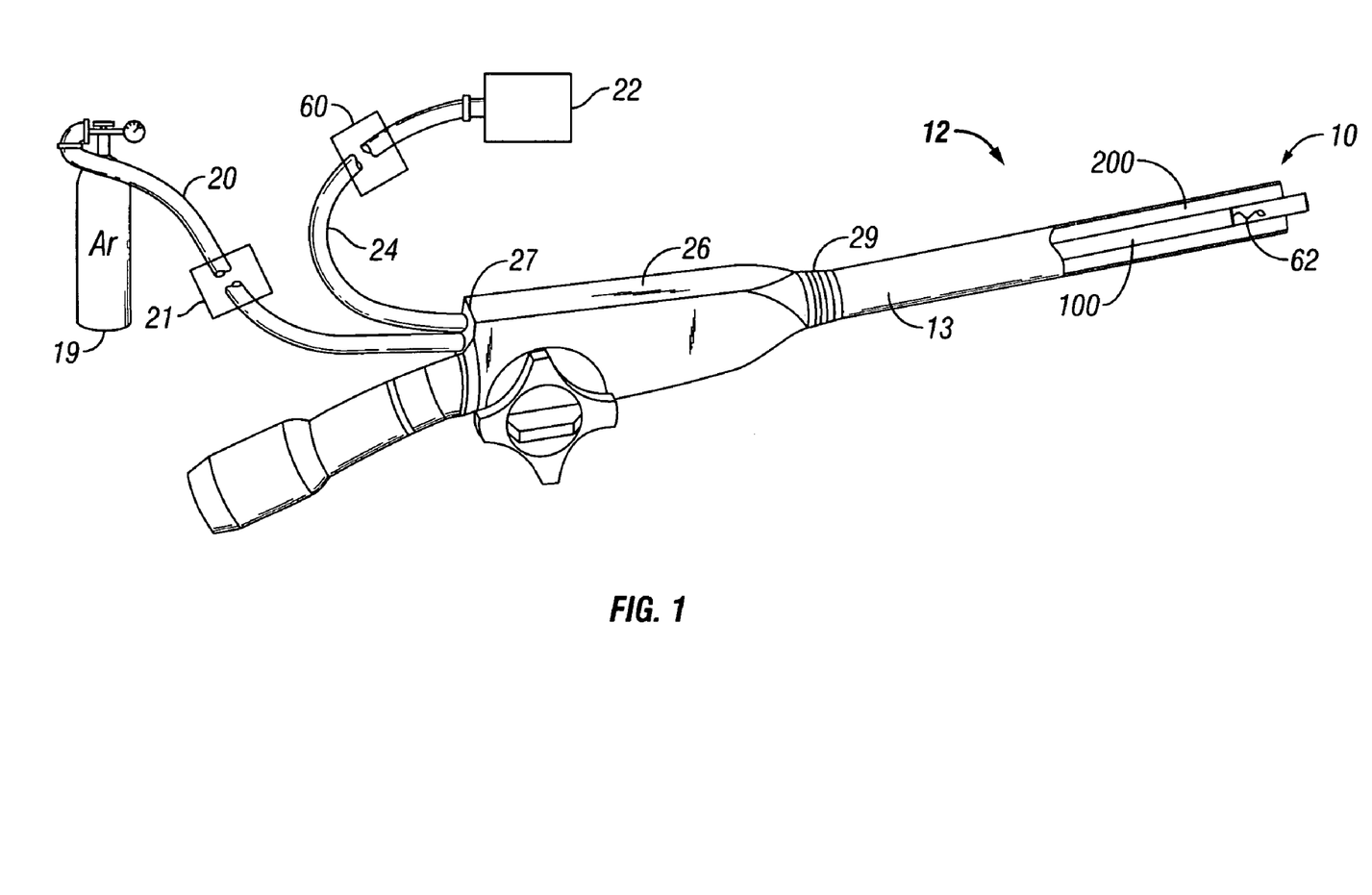
FIG. 1 is a perspective view of an electrosurgical instrument according to an embodiment of the present disclosure.

Referring to FIG. 1, a gas-enhanced tissue coagulator generally identified by reference numeral 10 is shown extending through a working channel of an endoscope 12. The coagulator 10 may be employed with a variety of suitable endoscopes, such as those manufactured by Olympus, Pentax and Fujinon. As such, only the basic operating features of the endoscope 12 that work in combination with the present disclosure need to be described herein.

Generally, the endoscope 12 includes a hand piece 26 having a proximal end 27 and a distal end 29. The proximal end 27 is mechanically coupled to a supply 19 of pressurized ionizable gas, e.g., inert gas, via hose 20 and electrically coupled to an electrosurgical generator 22 by way of cable 24 to supply electrosurgical energy, e.g., high frequency coagulation current, to the endoscope 12. The electrosurgical generator 22 may be configured to selectively control the amount of electrosurgical energy transmitted to an electrode during a surgical procedure. The supply 19 of pressurized ionizable gas may be configured to selectively control the rate of flow of gas, which is typically greater than 1 liter per minute.

Figure 2:
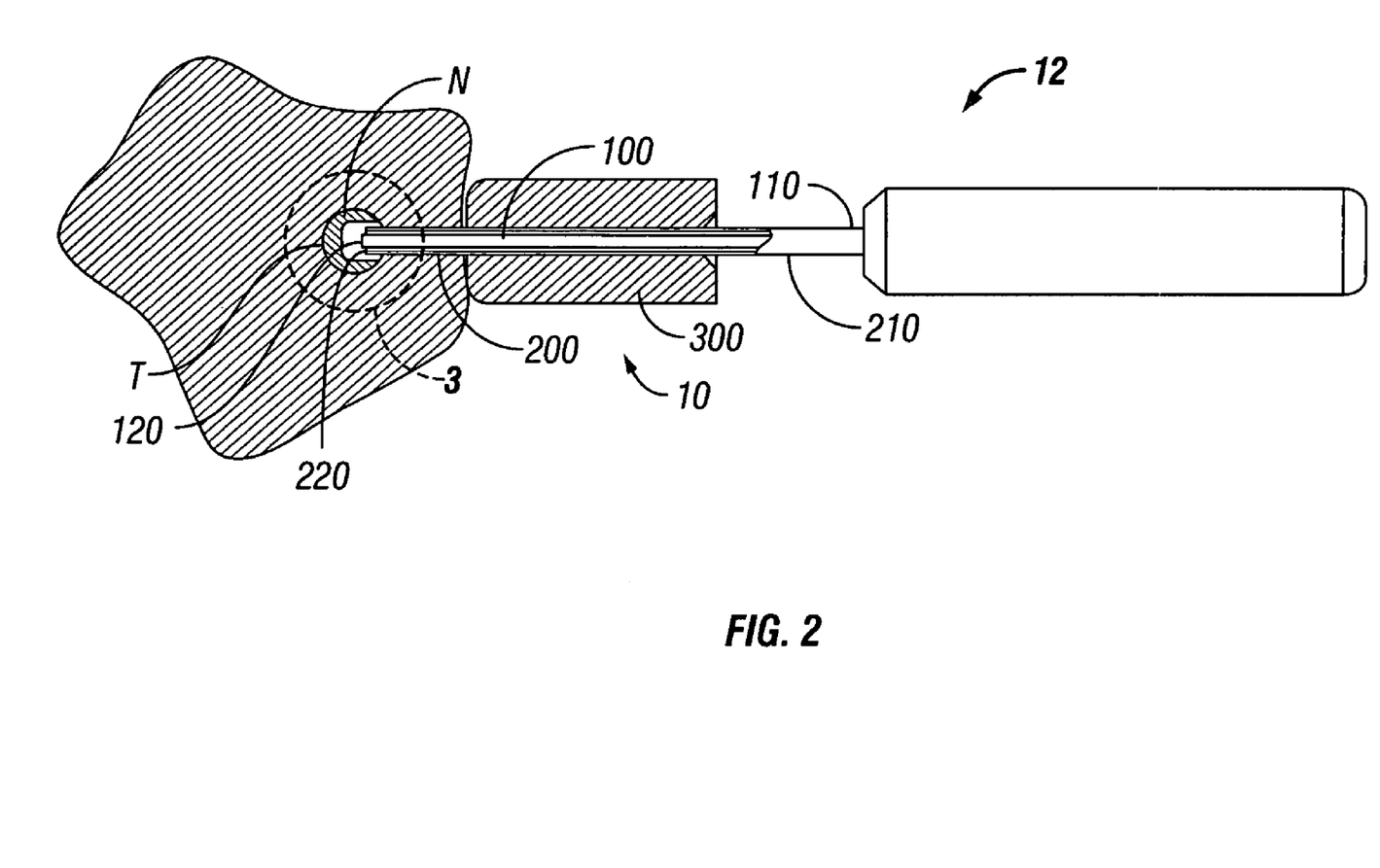
FIG. 2 is an enlarged, side sectional view of one embodiment of the present disclosure showing a first tube and a second tube inserted into tissue.
Figure 4:
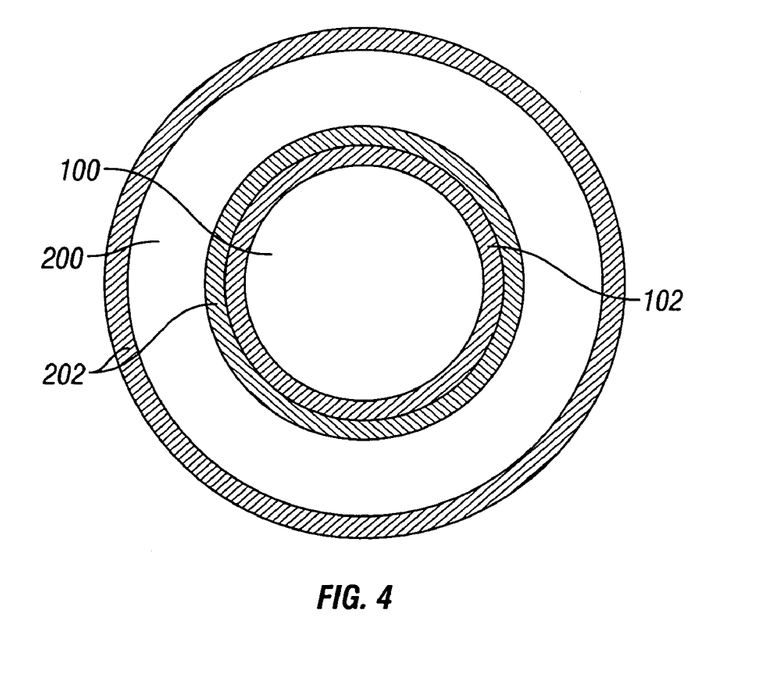
FIG. 4 is an end cross-sectional view of the first tube and the second tube according to one embodiment of the present disclosure.

As shown in FIGS. 1 and 2, a long, generally flexible tubular member 13 having a first tube 100 located within a second concentric tube 200 is mechanically coupled to the distal end 29 of the hand piece 26. First tube 100 includes a proximal end 110 and a distal end 120 and second tube 200 includes a proximal end 210 and a distal end 220. As best illustrated in FIG. 4, first tube 100 and second tube 200 are concentrically oriented, such that first tube 100 is disposed within second tube 200. First tube 100 and second tube 200 may include insulation coatings 102, 202, respectively, to electrically isolate tubes 100 and 200 from one another. Distal end 120 of the first tube 100 extends distally from the distal end 220 of the second tube 200, the purposes of which are explained in more detail below.

Turning now to FIG. 2, an enlarged, side sectional view of one embodiment of the coagulator 10 is shown. First tube 100 and second tube 200 are shown inserted into tissue, generally designated as "N." The first tube 100 is configured to deliver ionizable gas towards a treatment area "T" out of its distal end 120. The proximal end 110 of the first tube 100 is configured to receive ionizable gas from the supply 19. Second tube 200 is configured to remove or evacuate gas and/or waste from the treatment area "T" through distal end 220. The gas and/or waste exits through proximal end 210 and is typically collected in a known manner such as a suitable medical waste container or a waste containment system. An introducer 300 may be utilized to facilitate the insertion of the coagulator 10 into the tissue "N".

With continued reference to FIGS. 1 and 2, ionizable gas, e.g., argon, is supplied to the proximal end 110 of the first tube 100 by a gas conduit (not explicitly shown) located inside tubular member 13. Ionizable gas 19 may be supplied to the first tube 100 at a selectable, predetermined flow rate. The flow rate of the ionizable gas may be selectively adjustable and/or regulated via a pressure regulator 21 depending upon a particular purpose or a particular surgical condition.

Figure 5:
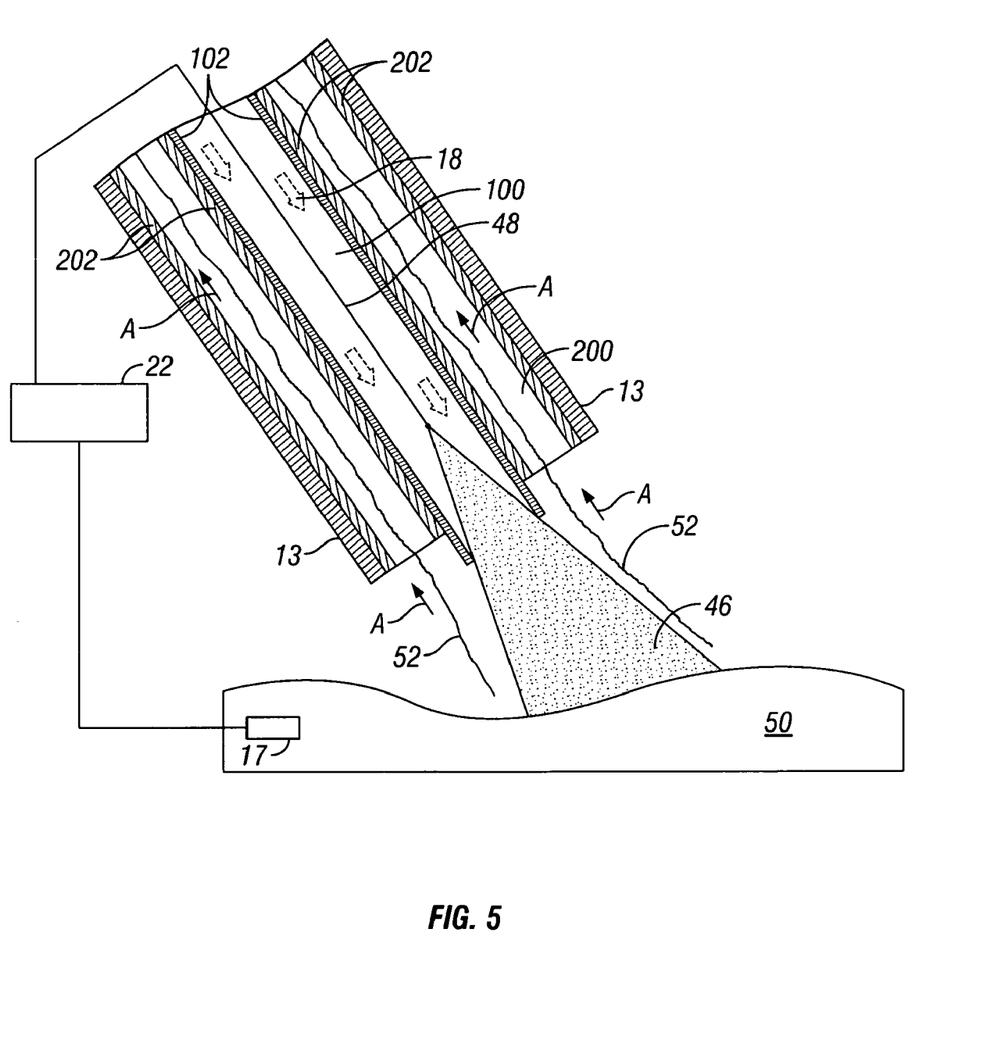
FIG. 5 is an enlarged, schematic sectional view of the first tube and the second tube illustrating ionized gas treating a tissue surface.

As mentioned above, the ionizable gas is supplied under pressure to the proximal end 110 of the first tube 100 and flows generally within the first tube 100 towards distal portion 120. An electrode 48 (see FIG. 5) discharges an electrosurgical current, e.g., radio frequency (RF), which ionizes the gas prior to the gas being expelled from the distal end 110 of the first tube 100 towards tissue "N." (Ionizable gas is illustrated as dashed arrows 18 in FIG. 5 and the resulting ionized gas is illustrated by the area designated as reference numeral 46.) The stream of ionized gas 46 conducts current to the tissue 50 while effectively scattering blood away from the treatment site allowing the tissue 50 to readily coagulate and arrest bleeding. The ionized gas 46 along with any vaporized material 52 is then suctioned away from the tissue (in the direction indicated by arrows A) through distal end 220 of second tube 200 via a suitable suctioning device (not explicitly shown). As best shown in FIG. 5, the generally wide ionized gas area allows a surgeon to effectively coagulate a wide tissue area. This is commonly referred to as a "coagulative painting."

Electrode 48 is connected by way of an electrical conduit disposed within the first tube 100, which is ultimately connected to the electrosurgical generator 22. The electrode 48 may be ring- or pin-type and is spaced from the distal opening 110 of the first tube 100 such that the electrode 48 does not come into contact with the tissue "N" or tissue 50 during the surgical procedure. In one embodiment of the present disclosure, an electrode control mechanism 60 allows an operator to control the current intensity to the electrode 48 during surgical procedures.

Ionizable gas 18 is controlled/manipulated such that it flows through the first tube 100 in a generally non-laminar or turbulent manner. However, various systems may be employed to cause the ionizable gas 18 to flow more or less turbulently or with other predetermined flow characteristics through the first tube 100. The gas flow may be used to cool tissue, thus reducing thermal margins or areas of ablated tissue during coagulation.

Figure 6:
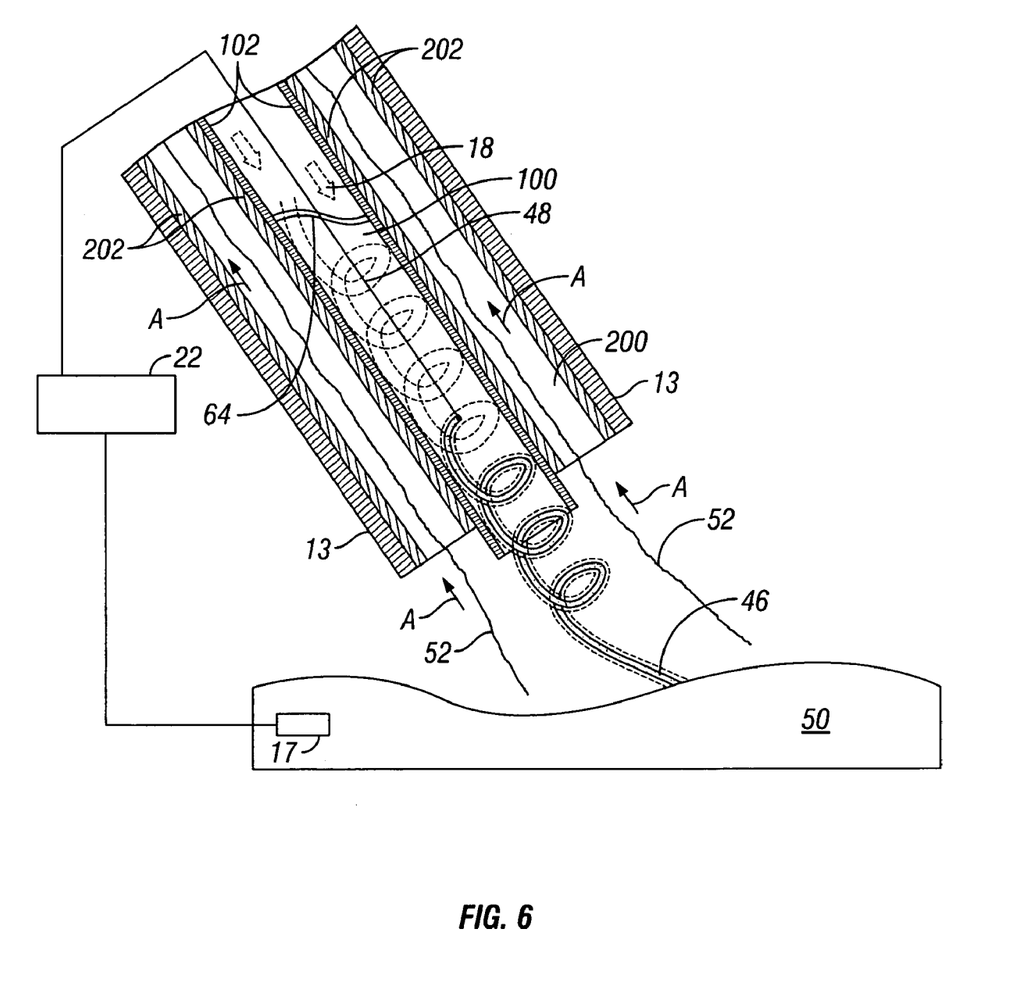
FIG. 6 is an enlarged, schematic sectional view of the first tube and the second tube illustrating a helically-shaped baffle located with the first tube for causing ionizable gas and/or ionized gas to exit the first tube with predetermined flow characteristics.

A fluid agitator, for example, such as a ribbon 62 (see FIG. 1), may be positioned within the first tube 100 to cause ionizable gas 18 and/or ionized gas 46 to swirl therewithin prior to the ionizable gas 18 and/or ionized gas 46 exiting the distal end 110 of the first tube 100. Additionally, with reference to FIG. 6, a generally helically-shaped baffle 64 may be positioned within the first tube 100 to cause ionizable gas 18 and/or ionized gas 46 to swirl within first tube 100 prior to the gas 18 or 46 exiting distal end 120 of first tube 100.

Figure 7A:
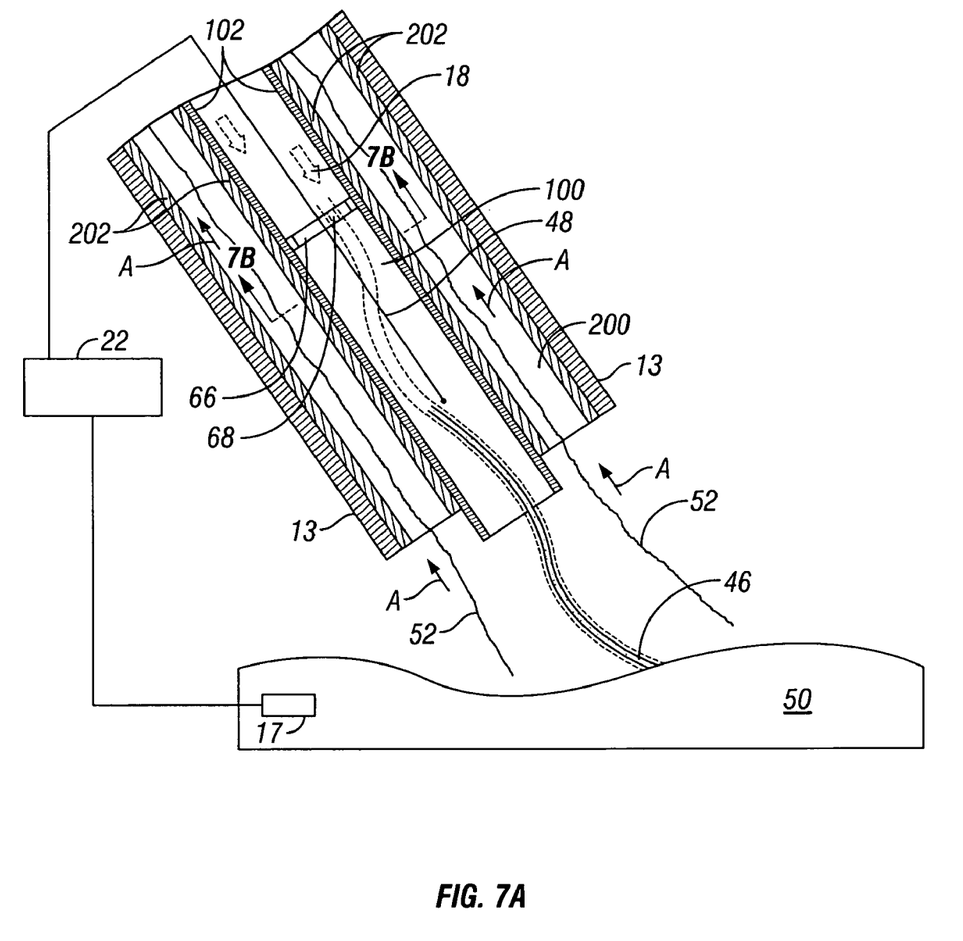
FIG. 7A is an enlarged, schematic sectional view of the first tube and the second tube wherein the first tube includes a rotating plenum having an aperture therein for causing ionizable gas and/or ionized gas to exit the first tube with predetermined flow characteristics.
Figure 7B:
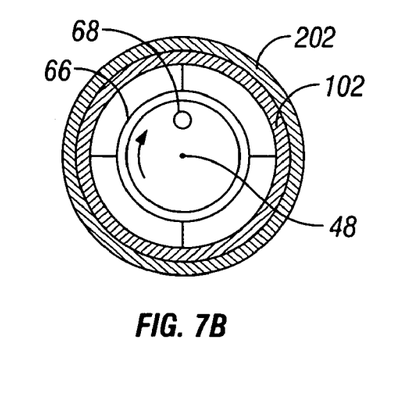
FIG. 7B is a cross-sectional view of the embodiment of FIG. 7A taken along line 7B-7B.

A rotatable plenum 66 is illustrated in FIGS. 7A and 7B, which includes at least one aperture 68 located therethrough. In this embodiment, the force of the ionizable gas 18 and/or ionized gas 46 flowing through aperture 68 causes the plenum 66 to rotate, which in turn causes the ionizable gas 18 and/or ionized gas 46 to swirl with predetermined flow characteristics. It is envisioned that the user can control the rotational speed of the plenum 66 by varying the pressure of ionizable gas 18 and/or ionized gas 46 flowing through first tube 100. It is also envisioned that the rotational speed of the plenum 66 is controlled by a separate mechanism that is independent of the ionizable gas 18 and/or ionized gas 46, e.g., a regulator (not explicitly shown).

Figure 8A:
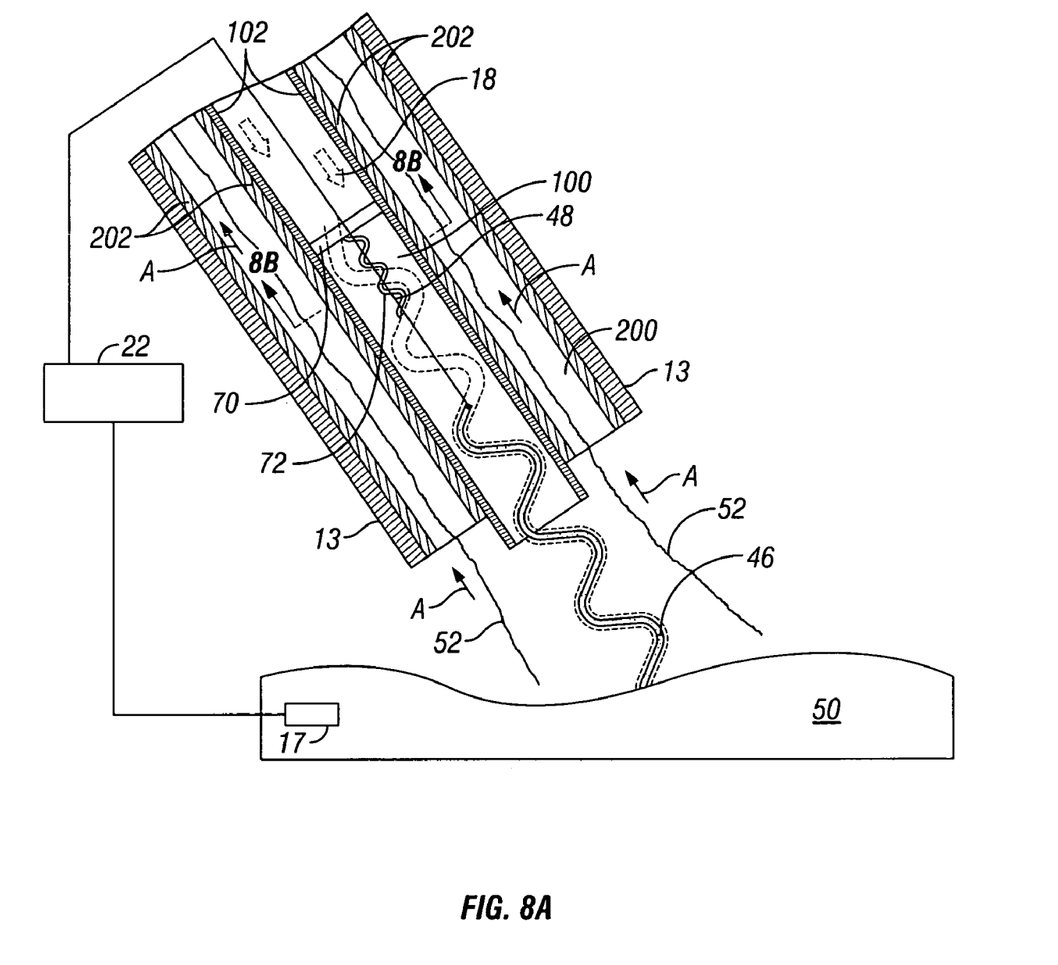
FIG. 8A is an enlarged, schematic sectional view of the first tube and the second tube wherein the first tube includes a pair of elongated flaps therein for causing ionizable gas and/or ionized gas to exit the first tube with predetermined flow characteristics.
Figure 8B:
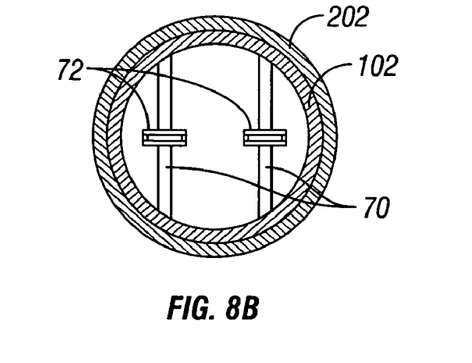

FIGS. 8A and 8B illustrate a flow system that includes a pair of rods 70 disposed within first tube 100 for supporting a pair of elongated flaps 72. Under flow conditions, flaps 72 attenuate/extend from rods 70 and flutter within the stream of ionizable gas 18 and/or ionized gas 46. It is envisioned that the force of ionizable gas 18 and/or ionized gas 46 flowing through first tube 100 causes each flap 72 to flutter, which in turn causes ionizable gas 18 and/or ionized gas 46 to move in a more turbulent manner. It is also envisioned that the rate/frequency of the flutter is directly related to the pressure of ionizable gas 18 and/or ionized gas 46 flowing through first tube 100. Any suitable number of flaps 72 can be employed to create certain flow conditions, e.g., a series of flaps 72 can be positioned at various positions along first tube 100 to create a more turbulent flow of ionizable gas 18 and/or ionized gas 46. Moreover, the length of each flap 72 may be varied to create additional flow effects.

Figure 3:
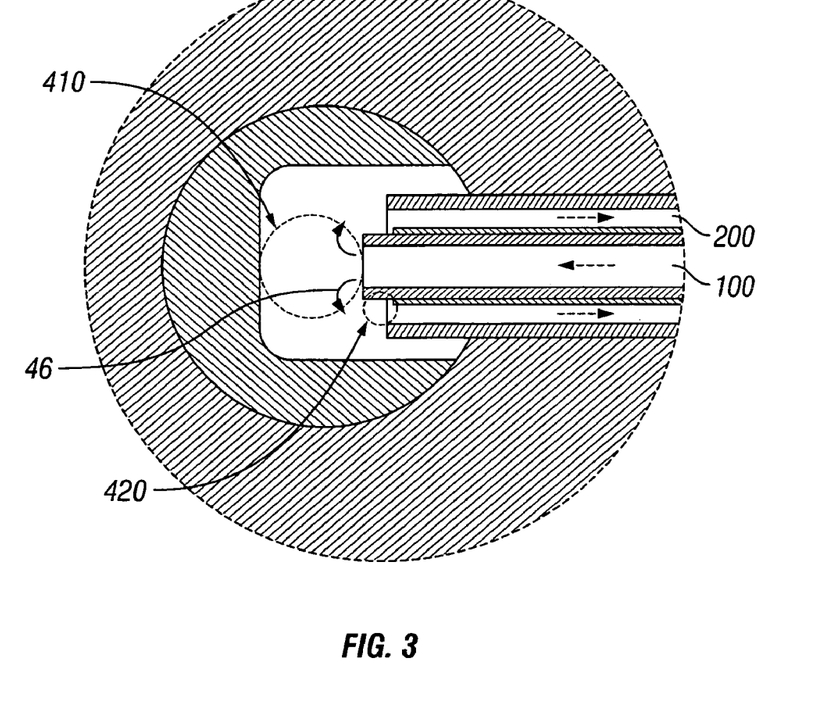
FIG. 3 is an enlarged, side sectional view of the area of detail shown in FIG. 2.

Coagulator 10 may be configured for monopolar and/or bipolar modes. In the monopolar mode, the first tube 100 may be the active electrode and a patient pad 17 (FIG. 5) may be the return electrode. In the monopolar mode, an arcing pattern 410 (FIG. 3) may radiate out from the distal end 120 of the first tube 100. In the bipolar mode, the first tube 100 may be the active electrode and the second tube 200 may be the return electrode. In the bipolar mode, the conductive path, represented by dashed lines 420, would be relatively self-contained at the distal end 120 of the first tube 100 due to the proximity of the active electrode and the return electrode. In one embodiment, monopolar and bipolar modes may be alternated a plurality of times per second during use, which would enable the conductive path in monopolar mode to arc into the surrounding tissue 50 causing desiccation and vaporization of the tissue 50 in close proximity to the distal end 120 of the first tube 100. The conductive path in bipolar mode further desiccates material that has been separated from the tissue 50 as the conductive path enters the second tube 200.

In operation, the introducer 300 may be inserted through the body and placed into tissue "N." A stylet (not shown) may facilitate the insertion of the introducer 300 into the tissue "N" by taking impedance readings. The stylet may then be removed upon confirmation of a desired impedance reading. Tubular member 13 of the coagulator 10 may then be inserted into the introducer 300, providing free access to the tissue "N." Once tubular member 13 is place in the tissue "N," the gas flow may be selectively initiated and the electrode 48 is thereafter selectively activated. A corona electrode may be used for inducing ignition of the ionizable gas 18. Ionized gas 46 flows out of the first tube 100 and is suctioned back into the second tube 200. When argon gas is used, the argon restricts the amount of tissue affected to the material that is adjacent the distal end 120 of the first tube 100. Nuclear material near the distal end 120 of the first tube 100 is thus vaporized and removed via the second tube 200.

From the foregoing and with reference to the various figures, those skilled in the art will appreciate that not only can the coagulator 10 of the present disclosure be used to arrest bleeding tissue, but the present disclosure can also be employed for desiccating and/or removing the surface tissue, eradicating cysts, forming eschars on tumors or thermically marking tissue. Those skilled in the art will also appreciate that certain modifications can be made to the present disclosure without departing from the scope of the present disclosure.

For example, the coagulator 10 of the present disclosure may include articulating qualities. In addition, tubular member 13, or at least a portion thereof, may have an arcuate shape. Moreover, the coagulator 10 of the present disclosure may be used while performing liposuction and/or for treating tumors. In such tumor-treating embodiments, a level of coagulation may be achieved and the second tube 200 may remove material, as opposed to coagulating the tissue and leaving it in the body. Furthermore, certain aspects of the present disclosure may be utilized with a portable device and a portable argon supply.

There is described and illustrated herein several embodiments of a gas-enhanced electrosurgical device that supplies gas to and removes gas from a treatment area. While particular embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of various embodiments. Those skilled in the art will envision other modifications within the scope and spirit of the claims appended hereto.

What is claimed is:

1. An electrosurgical apparatus for coagulating tissue, comprising:
   a first tube having a proximal end and a distal end, the proximal end being configured to receive pressurized ionizable gas and the distal end being configured to deliver ionized gas towards a treatment area;
   at least one electrode positioned to selectively ionize the pressurized ionizable gas prior to the pressurized ionizable gas exiting the distal end of the first tube, the electrode adapted to be operatively coupled to an electrical energy source; and
   a second tube having proximal and distal ends, the second tube being configured to selectively evacuate the ionized gas and dislodged tissue material from the treatment area, wherein the distal end of the first tube extends distally beyond the distal end of the second tube and wherein the distal end of the second tube extends distally beyond a distal end of the at least one electrode,
   wherein the electrosurgical apparatus is configured for use in a bipolar mode wherein the first tube is activated with a first electrical potential and the second tube is activated with a second electrical potential.

2. The electrosurgical apparatus according to claim 1, wherein the first tube is concentrically disposed within the second tube.

3. The electrosurgical apparatus according to claim 1, further comprising a regulator which regulates the flow of pressurized argon through the first tube, the regulator being disposed between a gas supply of the pressurized argon and the proximal end of the first tube.

4. The electrosurgical apparatus according to claim 3, further comprising a fluid agitator, the fluid agitator being configured to impart non-laminar flow characteristics to the pressurized ionizable gas.

5. The electrosurgical apparatus according to claim 4, wherein the fluid agitator is disposed within the first tube.

6. The electrosurgical apparatus according to claim 5, wherein the pressurized ionizable gas is used to cool tissue.

* * * * *